(12) United States Patent
Batista et al.

(10) Patent No.: US 11,857,722 B2
(45) Date of Patent: Jan. 2, 2024

(54) ASSEMBLY COMPRISING SHEET HEATING ELEMENT AND DELIVERY DEVICE

(71) Applicant: Altria Client Services LLC, Richmond, VA (US)

(72) Inventors: Rui Nuno Batista, Morges (CH); Dani Ruscio, Cressier (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 17/518,775

(22) Filed: Nov. 4, 2021

(65) Prior Publication Data

US 2022/0053832 A1 Feb. 24, 2022

Related U.S. Application Data

(63) Continuation of application No. 16/288,569, filed on Feb. 28, 2019, now Pat. No. 11,166,491, which is a
(Continued)

(30) Foreign Application Priority Data

Mar. 31, 2016 (EP) ..................... 16163418

(51) Int. Cl.
*A24F 40/10* (2020.01)
*A24F 40/46* (2020.01)
(Continued)

(52) U.S. Cl.
CPC .............. *A61M 15/06* (2013.01); *A24F 40/46* (2020.01); *A24F 40/48* (2020.01); *A24F 40/10* (2020.01); *A24F 40/50* (2020.01); *A24F 40/53* (2020.01)

(58) Field of Classification Search
CPC .......... A24F 40/10; A24F 40/46; A24F 40/48; A24F 40/50; A24F 40/53; A61M 11/006;
(Continued)

(56) References Cited

U.S. PATENT DOCUMENTS 5,666,977 A * 9/1997 Higgins ................. A24F 40/48
131/194
6,881,417 B1 * 4/2005 Laughlin ................ A61M 11/06
424/59
(Continued)

FOREIGN PATENT DOCUMENTS

| KR | 10-2013-0029697 A | 3/2013 | |
|---|---|---|---|
| WO | WO-2015/117704 A1 | 8/2015 | |
| WO | WO-2017167647 A1 * | 10/2017 | ............ A24F 40/10 |

OTHER PUBLICATIONS

Extended European Search Report dated Jun. 9, 2016 for corresponding European Application No. 16163418.3.
(Continued)

*Primary Examiner* — Hae Moon Hyeon
*Assistant Examiner* — Thang H Nguyen
(74) *Attorney, Agent, or Firm* — Harness, Dickey & Pierce, P.L.C.

(57) ABSTRACT

A vaporizing assembly for an aerosol generating system includes a sheet heating element and a delivery device configured to deliver a liquid aerosol-forming substrate from a liquid storing portion to the sheet heating element. The sheet heating element is spaced apart from the delivery device and is configured to heat the delivered liquid aerosol forming substrate.

12 Claims, 2 Drawing Sheets

Related U.S. Application Data continuation of application No. 15/474,136, filed on Mar. 30, 2017, now Pat. No. 10,244,795, which is a continuation of application No. PCT/EP2017/057015, filed on Mar. 23, 2017.

(51) Int. Cl.
    *A24F 40/50*     (2020.01)
    *A61M 15/06*     (2006.01)
    *A24F 40/48*     (2020.01)
    *A24F 40/53*     (2020.01)

(58) Field of Classification Search
CPC .. A61M 11/041; A61M 11/042; A61M 15/06; A61M 2205/3653; A61M 2205/50; A61M 2205/8206
See application file for complete search history.

(56) References Cited

U.S. PATENT DOCUMENTS

| | | | |
|---|---|---|---|
| 10,701,984 B2* | 7/2020 | Memari | B65D 25/005 |
| 2003/0062042 A1* | 4/2003 | Wensley | A61M 11/044 |
| | | | 128/203.12 |
| 2006/0196518 A1* | 9/2006 | Hon | H02J 7/00 |
| | | | 131/347 |
| 2008/0230052 A1 | 9/2008 | Montaser | |
| 2009/0289083 A1* | 11/2009 | Kamishita | A61M 11/007 |
| | | | 222/386 |
| 2013/0104916 A1* | 5/2013 | Bellinger | A61M 11/042 |
| | | | 131/328 |
| 2014/0190496 A1 | 7/2014 | Wensley et al. | |
| 2014/0283855 A1* | 9/2014 | Hawes | A24F 40/48 |
| | | | 131/328 |
| 2014/0305454 A1* | 10/2014 | Rinker | A24F 40/46 |
| | | | 131/329 |
| 2015/0034103 A1* | 2/2015 | Hon | A24F 40/44 |
| | | | 131/328 |
| 2015/0114409 A1 | 4/2015 | Brammer et al. | |
| 2016/0021931 A1* | 1/2016 | Hawes | F04B 19/006 |
| | | | 392/394 |
| 2016/0106154 A1* | 4/2016 | Lord | A24F 40/485 |
| | | | 392/395 |
| 2016/0106155 A1* | 4/2016 | Reevell | H05B 1/0297 |
| | | | 131/329 |
| 2016/0262456 A1* | 9/2016 | Borkovec | H05B 1/0244 |
| 2016/0262457 A1* | 9/2016 | Borkovec | A61M 15/002 |
| 2017/0020192 A1* | 1/2017 | Fregonese | A24F 40/485 |
| 2017/0128364 A1* | 5/2017 | Kamishita | B05B 1/34 |
| 2017/0280776 A1* | 10/2017 | Manca | H05B 3/44 |
| 2017/0280777 A1* | 10/2017 | Manca | H05B 3/265 |
| 2018/0279680 A1* | 10/2018 | Rashid | A24F 40/485 |
| 2018/0343921 A1* | 12/2018 | Daryani | B05B 1/24 |
| 2019/0261687 A1* | 8/2019 | Wensley | A24F 40/50 |
| 2020/0205474 A1* | 7/2020 | Tong | A24F 40/44 |

OTHER PUBLICATIONS

International Search Report for corresponding International Application No. PCT/EP2017/057015 dated Jun. 12, 2017.
International Preliminary Report on Patentability dated Mar. 21, 2018 in International Application No. PCT/EP2017/057015.
European Office Action for corresponding Application No. 17713012.7-1122—dated Nov. 25, 2019.
Russian Office Action and Search Report for Application No. 2018138201, dated Apr. 3, 2020.
Russian Notice of Allowance for corresponding Application No. 2018138201, dated Jul. 20, 2020.
Japanese Office Action dated Mar. 29, 2021, issued in corresponding Japanese Patent Application No. 2018-550585.
Japanese Office Action dated Aug. 23, 2021 for corresponding Japanese Application No. 2018-550585, and English-language translation thereof.
Korean Office Action dated May 26, 2022 for corresponding Korean Application No. 10-2018-7029332, and english-language translation thereof.
Japanese Notice of Allowance dated Jan. 13, 2022 for corresponding Japanese Application No. 2018-550585, and English-language translation thereof.

\* cited by examiner

ASSEMBLY COMPRISING SHEET HEATING ELEMENT AND DELIVERY DEVICE

CROSS-REFERENCE TO RELATED APPLICATIONS

This is a continuation application of U.S. application Ser. No. 16/288,569, filed Feb. 28, 2019, which is a continuation application of U.S. application Ser. No. 15/474,136, filed Mar. 30, 2017, which claims priority to PCT/EP2017/057015 filed on Mar. 23, 2017, and further claims priority to EP 16163418.3 filed on Mar. 31, 2016; the entire contents of each of which are hereby incorporated herein by reference in their entirety.

BACKGROUND

Aerosol generating systems may comprise a liquid storing portion for storing a liquid aerosol-forming substrate and an electrically operated vaporizer including a heating element for vaporizing the aerosol-forming substrate. An aerosol is generated when the vaporized aerosol-forming substrate condenses in an airflow passing the heating element. The liquid aerosol-forming substrate is supplied to the heating element by a wick having a set of fibers coupled to the liquid storing portion. It may be challenging to control the amount of aerosol-forming substrate that is supplied to the heating element and is to be incorporated in the generated aerosol.

It would be desirable to provide a vaporizing assembly for an aerosol generating system and a delivery system that provide some control of the amount of vaporized aerosol-forming substrate in the generated aerosol. Moreover, it would be desirable to achieve repeatability of generating an aerosol with a desired (or, alternatively a predetermined) amount of vaporized aerosol-forming substrate.

SUMMARY

At least one example embodiment relates to a vaporizing assembly for an aerosol generating system and a delivery system for evaporating a liquid aerosol-forming substrate. At least one example embodiment relates to handheld aerosol generating systems such as electrically operated aerosol generating systems.

In at least one example embodiment, a vaporizing assembly for an aerosol generating system comprises a heating element including a sheet heating element including a plurality of electrically conductive fibers; a liquid storing portion configured to store a liquid aerosol forming substrate therein; and a delivery device configured to deliver the liquid aerosol-forming substrate from the liquid storing portion to the heating element. The heating element is spaced apart from the delivery device. The heating element is configured to heat the delivered liquid aerosol forming substrate to form an aerosol In at least one example embodiment, an aerosol generating system comprises a vaporizing assembly and an operation unit configured to detect an operation to initiate aerosol generation. The vaporizing assembly includes a heating element including a sheet heating element; a liquid storing portion configured to store a liquid aerosol forming substrate therein; and a delivery device configured to deliver the liquid aerosol-forming substrate from the liquid storing portion to the heating element. The heating element is spaced apart from the delivery device. The heating element is configured to heat the delivered liquid aerosol forming substrate to form an aerosol.

BRIEF DESCRIPTION OF THE DRAWINGS

Example embodiments will now be described, by way of example only, with reference to the accompanying drawings.

Figure 1:
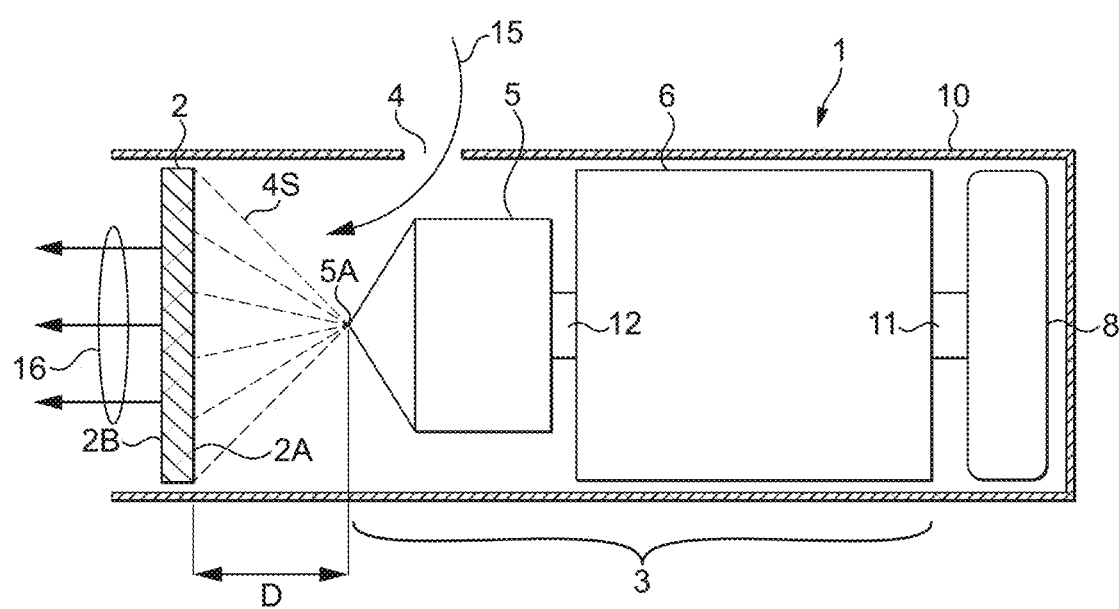
FIG. 1 is a schematic view of a vaporizing assembly in accordance with at least one example embodiment.

Throughout the figures, the same reference signs will be assigned to the same or similar components and features.

DETAILED DESCRIPTION

Various example embodiments will now be described more fully with reference to the accompanying drawings in which some example embodiments are shown. However, specific structural and functional details disclosed herein are merely representative for purposes of describing example embodiments. Thus, the embodiments may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

In order to more specifically describe example embodiments, various features will be described in detail with reference to the attached drawings. However, example embodiments described are not limited thereto.

In at least one example embodiment, a vaporizing assembly for an aerosol generating system comprises a sheet heating element and a delivery device configured to deliver a liquid aerosol-forming substrate from a liquid storing portion to the sheet heating element. The sheet heating element is spaced apart from the delivery device and is configured to heat the delivered liquid aerosol-forming substrate to a temperature sufficient to volatilize at least a part of the delivered liquid aerosol-forming substrate. The sheet heating element is fluid permeable and comprises a plurality of electrically conductive filaments.

As used herein, a sheet heating element comprises a thin, substantially flat, electrically conductive material, such as a mesh of fibers, a conductive film, or an array of heating strips, suitable for receiving and heating an aerosol forming substrate for use in an aerosol generating system.

As used herein, "thin" means about 8 micrometers to about 2 millimeters, about 8 micrometers to about 500 micrometers, or about 8 micrometers to about 100 micrometers. In the case of a mesh made up of filaments, the filaments may have a diameter of less than about 40 micrometers.

As used herein, "substantially flat" means having a planar profile, such that it can be disposed in the vaporizing assembly spaced apart from the delivery device and receive a jet or spray from the device substantially uniformly across the heating element. However, in some example embodiments, the sheet heating element may be curved in order to optimize the delivery of the substrate, depending on the characteristics of the delivery distribution of the delivery device. Accordingly, the "substantially flat" characteristic of the sheet heating element pertains to the form of the element in its manufacture, but not necessarily to its arrangement in the vaporizing assembly. In at least one example embodiment, the sheet heating element is also in a substantially flat orientation in the vaporizing assembly, spaced and opposed from the delivery device.

As used herein, "electrically conductive" means formed from a material having a resistivity of about $1\times10^{-4}$ ohm meters, or less.

The sheet heating element comprises a plurality of openings. In at least one example embodiment, the sheet heating element may comprise a mesh of fibers with interstices between them. The sheet heating element may comprise a thin film or plate, optionally perforated with small holes. The sheet heating element may comprise an array of narrow heating strips connected in series.

The sheet heating element has a surface area of less than or equal to about 100 square millimeters, allowing the sheet heating element to be incorporated in to a handheld system. The sheet heating element may, have a surface area of less than or equal to about 50 square millimeters.

In at least one example embodiment, electrically conductive filaments are arranged in a mesh to form the sheet heating element, having a size ranging from about 160 Mesh US to about 600 Mesh US (+/−10%) (e.g., ranging from about 400 filaments per centimeter to about 1500 filaments per centimeter (+/−10%)). The width of the interstices ranges from about 10 micrometers to about 200 micrometers, or from about 25 micrometers to about 75 micrometers. The percentage of open area of the mesh, which is the ratio of the area of the interstices to the total area of the mesh, ranges from about 25 percent to about 56 percent. The mesh may be formed using different types of weave or lattice structures. In at least one example embodiment, the electrically conductive filaments consist of an array of filaments arranged parallel to one another.

In at least one example embodiment, an electrically conductive film or plate may form the sheet heating element. The film or plate may be made of metal, conductive plastic, or other appropriate conductive material. In at least one example embodiment, the plate of film is perforated with holes that have a size on the order of interstices as described in the mesh embodiment above.

In at least one example embodiment, narrow heating strips may be combined in an array to form the sheet heating element. The smaller the width of the heating strips in an array, the more heating strips may be connected in series in the sheet heating element of the present invention. When using smaller width heating strips that are connected in series, the electric resistance of their combination into the sheet heating element is increased.

The delivery device comprises an inlet and an outlet. The delivery device is configured to receive a liquid aerosol forming substrate at an inlet and to output, at an outlet, an amount of the liquid aerosol forming substrate to be delivered to the sheet heating element.

The sheet heating element is configured to heat the delivered liquid aerosol-forming substrate to a temperature sufficient to volatilize at least a part of the delivered liquid aerosol-forming substrate.

The sheet heating element is spaced apart from the delivery device. As used herein, "spaced apart" means that the vaporizing assembly is configured to deliver the liquid aerosol-forming substrate from the delivery device via an air gap to the sheet heating element. Spaced apart also means that the delivery device and the sheet heating element are not coupled by a tubing segment for leading flow of the liquid aerosol forming substrate from the delivery device to the heating element. Spaced apart may also mean that the delivery device and the sheet heating element are provided as individual members separated from each other by an air gap. The term spaced apart includes an integral combination of the delivery device and the sheet heating element into a combined component as long as the liquid aerosol-forming substrate has to pass through an air gap within this combined component immediately before being heated by the sheet heating element.

By providing the sheet heating element spaced apart from the delivery device, the amount of liquid aerosol forming substrate delivered to the heating element may be better controlled compared to a vaporizer having a tubing segment configured to lead flow of the liquid aerosol forming substrate from the delivery device to the heating element. Capillary actions due to use of a tubing segment may be avoided which might otherwise, for example, give rise to movement of liquid between the heating element and the delivery device. When passing the air gap the delivered amount of the liquid aerosol-forming substrate may be transformed into a jet of droplets before hitting the surface of the sheet heating element. Thus, a uniform distribution of the delivered amount of the liquid aerosol forming substrate on the sheet heating element may be enhanced, leading to better controllability and repeatability of generating an aerosol with a desired (or, alternatively predetermined) amount of vaporized aerosol forming substrate per inhalation cycle.

The operating temperature of the sheet heating element may range from about 120 degrees Celsius to about 210 degrees Celsius, or from about 150 degrees Celsius to about 180 degrees Celsius.

The sheet heating element comprises a plurality of electrically conductive filaments. In at least one example embodiment, the sheet heating element is a mesh heating element, comprising the plurality of electrically conductive filaments. The plurality of electrically conductive filaments forms a mesh of the mesh heating element. The mesh is heated by applying electric power to the plurality of electrically conductive filaments. The sheet heating element may comprise a plurality of filaments which can be made of a single type of fibers, such as resistive fibers, as well as a plurality of types of fibers, including capillary fibers and conductive fibers.

The electrically conductive filaments may comprise any suitable electrically conductive material. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. The filaments may be coated with one or more insulators. The electrically conductive filaments made be formed of 304, 316, 304L, and 316L stainless steel, and graphite.

The electrical resistance of the plurality of electrically conductive filaments of the mesh heating element may range from about 0.3 Ohms to about 4 Ohms. In at least one example embodiment, the electrical resistance of the plurality of electrically conductive filaments ranges from about 0.5 Ohms to about 3 Ohms, or about 1 Ohm. The electrical resistance of the plurality of electrically conductive filaments is at least an order of magnitude, or at least two orders of magnitude, greater than the electrical resistance of electrical contact portions of the mesh heating element. This ensures that the heat generated by passing current through the mesh heating element is localized to the plurality of electrically conductive filaments.

The electrically conductive filaments may define interstices between the filaments and the interstices may have a width ranging from about 10 micrometers to about 100 micrometers. In at least one example embodiment, the filaments give rise to capillary action in the interstices, so that liquid to be vaporized is drawn into the interstices thereby increasing the contact area between the heater assembly and the liquid.

The mesh of electrically conductive filaments may also be characterized by its ability to retain liquid.

In at least one example embodiment, the mesh heating element comprises at least one filament made from a first material and at least one filament made from a second material different from the first material. This may be beneficial for electrical or mechanical reasons. In at least one example embodiment, one or more of the filaments may be formed from a material having a resistance that varies significantly with temperature, such as an iron aluminum alloy. This allows a measure of resistance of the filaments to be used to determine temperature or changes in temperature. This can be used in a puff detection system and for controlling temperature of the heating element to keep it within a desired temperature range.

The sheet heating element is fluid permeable. As used herein, fluid permeable in relation to a sheet heating element means that the aerosol forming substrate, in a gaseous phase and possibly in a liquid phase, can readily pass through the sheet heating element. Including a fluid permeable heater may enhance surface area and improve vaporization. In addition, a fluid permeable heater may also allow improved mixing of vaporized liquid aerosol forming substrate with an air flow.

In at least one example embodiment, the sheet heating element is substantially flat. As used herein, substantially flat means formed in a single plane and not wrapped around or other conformed to fit a curved or other non-planar shape. A flat heating element can be easily handled during manufacture and provides for a robust construction.

In at least one example embodiment, where the sheet heating element is a mesh heating element, the mesh heating element may comprise a plurality of mesh layers stacked in an intended direction of airflow through the mesh heating element. Each mesh layer can be easily handled during manufacture and provides for a robust construction. Moreover, the stacked mesh layers improve vaporization of the liquid aerosol forming substrate.

In at least one example embodiment, the sheet heating element has a square geometry. The sheet heating element may have a heating area with a square geometry with dimensions of each side within a range of about 3 millimeters to about 7 millimeters, or from about 4 millimeters to about 5 millimeters.

The sheet heating element may comprise a plurality of narrow heating strips arranged spaced apart from each other on a plane. The heating strips are in a rectangular shape and spatially arranged substantially parallel to each other. The heating strips may be electrically connected in series. By appropriate spacing of the heating strips, a more even heating may be obtained compared with for example where a sheet heating element having the same area is used.

In at least one example embodiment, the delivery device is configured to deliver a desired (or, alternatively predetermined) amount of the liquid aerosol-forming substrate to the sheet heating element upon performing one activation cycle. The desired (or, alternatively predetermined) amount of the liquid aerosol-forming substrate is delivered via the air gap from the delivery device to the sheet heating element. By depositing the liquid aerosol-forming substrate onto the sheet heating element directly, the liquid aerosol-forming substrate may remain substantially in its liquid state until it reaches the sheet heating element, although small droplets near the element may aerosolize before contacting the sheet heating element. The desired (or, alternatively predetermined) amount of the liquid aerosol-forming substrate may be an amount equivalent to produce a desired volume of aerosol in the sheet heating element.

In at least one example embodiment, the delivery device is configured to spray the liquid aerosol forming substrate onto the sheet heating element as a spraying jet with a size and shape appropriate to the geometry of the sheet heating element. The delivery device may be configured to spray the liquid aerosol forming substrate onto the sheet heating element to cover at least 90 percent or at least 95 percent, of an upstream surface of the sheet heating element facing the delivery device.

The delivery device may comprise an atomizer spray nozzle, in which case a flow of air is supplied through the nozzle by the action of puffing, which creates a pressurized air flow that will mix and act with the liquid creating an atomized spray in the outlet of the nozzle. Several systems including nozzles that work with small volumes of liquid are available, in sizes that meet the requirements to fit in small portable devices. Another class of nozzle that may be used is an airless spray nozzle, sometimes referred to as a micro-spray nozzle. Such nozzles create micro spray cones in very small sizes. With this class of nozzles, the airflow management inside the device, namely inside the mouth piece, surrounds the nozzle and the heating element, flushing the heating element surface towards the outlet of the mouth piece, including a turbulent air flow pattern of the aerosol exiting the mouth piece.

For either class of nozzle, the distance of the air gap between the delivery device and the sheet heating element facing the nozzle, is within a range of from about 2 millimeters to about 10 millimeters, or from about 3 millimeters to about 7 millimeters. Any type of available spraying nozzles may be used. Airless nozzle 062 Minstac from manufacturer "The Lee Company" is an example of a suitable spray nozzle.

In at least one example embodiment, the delivery device comprises a micropump configured to pump the liquid aerosol-forming substrate from a liquid storage portion. By using the micropump instead of a capillary wick or any other passive medium to draw liquid, only the actually required amount of liquid aerosol-forming substrate may be transported to the sheet heating element. Liquid aerosol-forming substrate may only be pumped upon demand, for example in response to a puff.

The micropump may allow on-demand delivery of liquid aerosol-forming substrate at a flow rate of about 0.7 microliters per second to about 4.0 microliters per second for intervals of variable or constant duration. A pumped volume of one activation cycle may be around 0.5 microliters in micropumps working within a pumping frequency ranging from about 8 hertz to about 15 hertz. In at least one example embodiment, the pump volume in each activation cycle, as a dose of liquid aerosol-forming substrate per puff, may be of 0.4 microliters to about 0.5 microliters.

The micropump may be configured to pump liquid aerosol-forming substrates that have a relatively high viscosity as compared to water. The viscosity of a liquid aerosol-forming substrate may be in the range from about 15 millipascal seconds to about 500 millipascal seconds, or in the range from about 18 millipascal seconds to about 81 millipascal seconds.

In some example embodiments, the delivery device may comprise a manually operated pump for pumping the liquid aerosol-forming substrate from a liquid storage portion. A manually operated pump reduces the number of electric and electronic components and thus, may simplify the design of the vaporizing assembly.

In at least one example embodiment, a vaporizing assembly suitable for an aerosol generating system comprises a sheet heating element and a delivery device configured to deliver a liquid aerosol-forming substrate from a liquid storing portion to the sheet heating element. The sheet heating element is spaced apart from the delivery device and is configured to heat the delivered liquid aerosol-forming substrate to a temperature sufficient to volatilize at least a part of the delivered liquid aerosol-forming substrate.

In at least one example embodiment, an aerosol generating system comprises the vaporizing assembly and an operation detection unit configure to detect an operation to initiate aerosol generation. The operation detection unit may include a puff detection system, e.g. a puff sensor. In at least one example embodiment, the operation detection unit may include an on-off button, e.g. an electrical switch. The on-off button may be configured to trigger activation of at least one of the micropump and the heating element when being pressed down. A duration of the on-off button being pressed down may determine the duration of activation of at least one of the micropump and the heating element, e.g. by constantly pressing down the on-off button during a puff.

In at least one example embodiment, the aerosol generating system further comprises a control unit which is configured to activate the delivery device with a desired (or, alternatively predetermined) time delay after activating the heating element in response to a detected user operation. Upon activation, such as using the on-off button or the puff sensor, the control unit may activate the sheet heating element first, and then, after delay of about 0.3 seconds to about 1 seconds, or from 0.5 seconds to about 0.8 seconds, may activate the delivery device. The duration of activation may be fixed or may correspond to an action like pressing the on-off button or puffing as, for example, detected by the operation detection unit. In at least one example embodiment, the control unit may be configured to activate the sheet heating element and the delivery device simultaneously.

In at least one example embodiment, the aerosol generating system may comprise a device portion and a replaceable liquid storage portion. The device portion may comprise a power supply and the control unit. The power supply may be any type of electric power supply, typically a battery. The power supply for the delivery device may be different from the power supply of the sheet heating element or may be the same.

The aerosol generating system may further comprise electric circuitry connected to the vaporizing assembly and to the power supply which is an electrical power source. The electric circuitry may be configured to monitor the electrical resistance of the sheet heating element, and to control the supply of power to the sheet heating element dependent on the electrical resistance of the sheet heating element.

The electric circuitry may comprise a controller with a microprocessor, which may be a programmable microprocessor. The electric circuitry may comprise further electronic components. The electric circuitry may be configured to regulate a supply of power to the vaporizing assembly. Power may be supplied to the vaporizing assembly continuously following activation of the system or may be supplied intermittently, such as on a puff-by-puff basis. The power may be supplied to the vaporizing assembly in the form of pulses of electrical current.

The power supply may be a form of charge storage device such as a capacitor, a super-capacitor, or hyper-capacitor. The power supply may require recharging and may have a capacity that allows for the storage of enough energy; for example, the power supply may have sufficient capacity to allow for the continuous generation of aerosol for a period of around six minutes or for a period that is a multiple of six minutes. In at least one example embodiment the power supply may have sufficient capacity to allow for a desired (or, alternatively predetermined) number of puffs or discrete activations of the vaporizing assembly.

For allowing air to enter the aerosol generating system, a wall of the housing of the aerosol generating system, such as a wall opposite the vaporizing assembly or a bottom wall, is provided with at least one semi-open inlet. The semi-open inlet allows air to enter the aerosol generating system, but does not allow air or liquid to leave the aerosol generating system through the semi-open inlet. A semi-open inlet may be a semi-permeable membrane, permeable in one direction only for air, but is air- and liquid-tight in the opposite direction. A semi-open inlet may also be a one-way valve. In at least one example embodiment, the semi-open inlets allow air to pass through the inlet only if specific conditions are met, for example a reduced and/or minimum depression in the aerosol generating system or a volume of air passing through the valve or membrane.

The liquid aerosol-forming substrate is a substrate that releases volatile compounds that can form an aerosol. The volatile compounds may be released by heating the liquid aerosol-forming substrate. The liquid aerosol-forming substrate may comprise plant-based material. The liquid aerosol-forming substrate may comprise tobacco. The liquid aerosol-forming substrate may comprise a tobacco-containing material containing volatile tobacco flavor compounds, which are released from the liquid aerosol-forming substrate upon heating. The liquid aerosol-forming substrate may alternatively comprise a non-tobacco-containing material.

The liquid aerosol-forming substrate may comprise homogenized plant-based material. The liquid aerosol-forming substrate may comprise homogenized tobacco material.

The liquid aerosol-forming substrate may comprise at least one aerosol-former. The liquid aerosol-forming substrate may comprise other additives and ingredients, such as flavorants.

The aerosol generating system may be an electrically operated system. In at least one example embodiment, the aerosol generating system is portable. The aerosol generating system may have a size comparable to a cigar or cigarette. The system may have a total length ranging from about 45 millimeters to about 160 millimeters. The system may have an external diameter ranging from about 7 millimeters to about 25 millimeters.

At least one example embodiment relates to a method for generating an aerosol. The method comprises heating a sheet heating element; and delivering, by a delivery device spaced apart from the sheet heating element, a liquid aerosol-forming substrate to the sheet heating element. The delivered liquid aerosol-forming substrate is heated by the sheet heating element to a temperature sufficient to volatilize at least a part of the delivered liquid aerosol-forming substrate.

Features described in relation to one aspect may equally be applied to other aspects of the invention.

In at least one example embodiment, as shown in FIG. 1, a vaporizing assembly 1 comprises a sheet heating element 2 and a delivery device 3 incorporated into a common housing 10. The delivery device 3 includes a micropump 6 and a spray nozzle 5 connected by a tubing segment 12. The micropump 6 is configured to receive, via the tubing segment 11, a liquid aerosol forming substrate from a replaceable liquid storing portion 8. The delivery device 3 is spaced apart from the mesh heater element 2. The delivery device 3 and the mesh heater element 2 are separated by an air gap having a length D between an outlet 5A of the spray nozzle 5 and the upstream surface 2A of the sheet heating element 2 facing the spray nozzle 5. The spray nozzle 5 is configured to receive an amount of the liquid aerosol forming substrate pumped from the micropump 6 via tubing segment 12 and to spray the amount of liquid aerosol forming substrate as a spraying jet 4S onto the upstream surface 2A of the sheet heating element 2. The spray nozzle 5 is configured to generate the spraying jet 4S such that the amount of liquid aerosol-forming substrate is completely received by the sheet heating element 2 and covers the entire upstream surface 2A of the sheet heating element 2. The housing 10 comprises an air inlet 4 allowing air 15 to pass from outside the housing 10 into the vaporizing assembly 1 towards the upstream surface 2A of the sheet heating element 2. The sheet heating element 2 is configured to allow the air 15 that enters from air inlet 4 to pass towards a downstream surface 2B of the sheet heating element 2 opposite from the spray nozzle 5. Having passed through the sheet heating element 2, the air 15 combines with the aerosol forming substrate vaporized by the sheet heating element 2 to form an aerosol 16.

Figure 2:
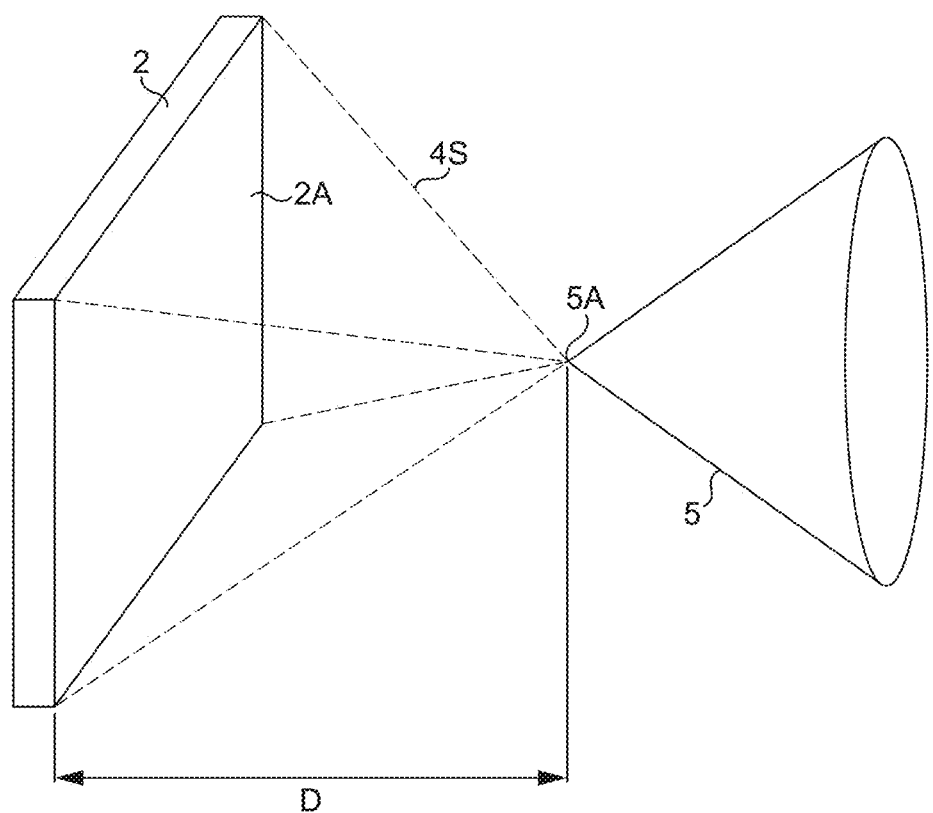
FIG. 2 is a schematic illustration of a spraying jet generated by a vaporizing assembly in accordance with at least one example embodiment.

In at least one example embodiment, as shown in FIG. 2, a spraying jet is generated by a vaporizing assembly. The spraying jet 4S output from the outlet 5A of the spray nozzle 5 of the vaporizing assembly illustrated in FIG. 1 has a size and shape fitted to the geometry of the upstream surface 2A of the sheet heating element 2. The upstream surface 2A has a square shape. The spraying jet 4S exhibits substantially the same square shape. The size of the spraying jet 4S arriving at the upstream surface 2A is the same as the size of the upstream surface 2A.

Figure 3:
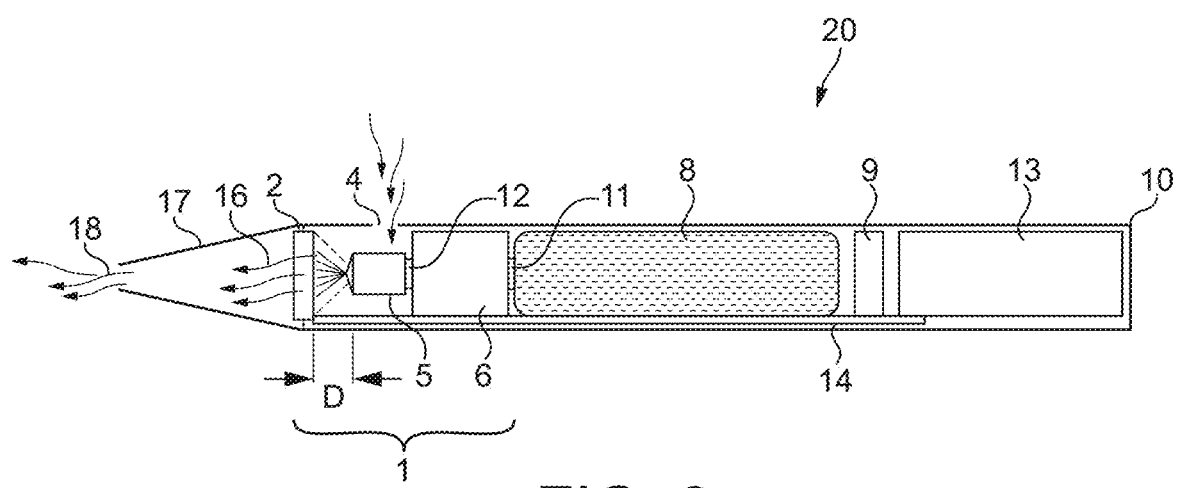
FIG. 3 is a schematic view of an aerosol generating system in accordance with at least one example embodiment.

In at least one example embodiment, as shown in FIG. 3, an aerosol generating system 20 comprises the vaporizing assembly 1 as illustrated in FIG. 1 and is configured to generate a spraying jet as shown in FIG. 2. Moreover, the aerosol generating system 20 comprises a liquid storing portion embodied by a replaceable container 8, an electronic control unit 9, a battery unit 13, wiring components 14 for electrically connecting the battery unit 13, the electronic control unit 9 and the electrically driven components of the vaporizing assembly 1, i.e. the sheet heating element 2 and the micropump 6. A replaceable mouth piece 17 having an air flow outlet 18 is coupled to the housing 10.

Various modifications and variations of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are apparent to those skilled in the mechanical arts, electrical arts, and aerosol generating article manufacturing or related fields are intended to be within the scope of the following claims.

We claim:

1. An assembly for an aerosol generating system, the assembly comprising:
   a heating element;
   a liquid storing portion configured to store a liquid aerosol-forming substrate therein; and
   a delivery device configured to deliver the liquid aerosol-forming substrate from the liquid storing portion to the heating element, the delivery device between the liquid storing portion and the heating element, the delivery device and the heating element defining an air gap therebetween, the delivery device including,
   a micropump, and
   an airless spray nozzle, the micropump configured to deliver the liquid aerosol-forming substrate from the liquid storing portion to the heating element via the airless spray nozzle, the airless spray nozzle configured to generate a spraying jet, such that an amount of the liquid aerosol-forming substrate sprayed by the airless spray nozzle is completely received by the heating element.

2. The assembly according to claim 1, wherein the air gap ranges from 2 millimeters to 10 millimeters in length.

3. The assembly according to claim 1, wherein the heating element is a mesh heater.

4. The assembly according to claim 3, wherein the heating element has a rectangular geometry.

5. The assembly according to claim 4, wherein the heating element has a square geometry.

6. The assembly according to claim 3, wherein the delivery device is configured to spray the liquid aerosol-forming substrate onto the heating element as a spray having a size and shape fitted to a geometry of the heating element.

7. An aerosol generating system, comprising:
   an assembly including,
   a heating element,
   a liquid storing portion configured to store a liquid aerosol-forming substrate therein, and
   a delivery device configured to deliver the liquid aerosol-forming substrate from the liquid storing portion to the heating element, the delivery device between the liquid storing portion and the heating element, the delivery device and the heating element defining an air gap therebetween, the delivery device including,
   a micropump, and an airless spray nozzle, the micropump configured to deliver the liquid aerosol-forming substrate from the liquid storing portion to the heating element via the airless spray nozzle, the airless spray nozzle configured to generate a spraying jet, such that an amount of the liquid aerosol-forming substrate sprayed by the airless spray nozzle is completely received by the heating element; and a device portion including,
   a power supply and configured to selectively supply power to the heating element from the power supply.

8. The aerosol generating system according to claim 7, further comprising:
   a control unit configured to activate the delivery device with a time delay after activating the heating element.

9. The aerosol generating system according to claim 8, therein the power supply includes the control unit.

10. The aerosol generating system according to claim 7, wherein the heating element is a mesh heater.

11. The aerosol generating system according to claim 10, wherein the heating element has a rectangular geometry.

12. The aerosol generating system according to claim 11, wherein the heating element has a square geometry.

* * * * *